(12) United States Patent
Chen

(10) Patent No.: US 8,642,736 B2
(45) Date of Patent: Feb. 4, 2014

(54) CASEIN COMPLEXES

(75) Inventor: Chyi-Cheng Chen, Taipei (TW)

(73) Assignee: DSM IP Assets B. V., Heerlen (NL)

( * ) Notice: Subject to any disclaimer, the term of this patent is extended or adjusted under 35 U.S.C. 154(b) by 755 days.

(21) Appl. No.: 12/375,974

(22) PCT Filed: Aug. 2, 2007

(86) PCT No.: PCT/EP2007/006821
§ 371 (c)(1),
(2), (4) Date: Nov. 4, 2009

(87) PCT Pub. No.: WO2008/017415
PCT Pub. Date: Feb. 14, 2008

(65) Prior Publication Data
US 2010/0099607 A1  Apr. 22, 2010

(30) Foreign Application Priority Data
Aug. 9, 2006 (EP) .................................. 06016660

(51) Int. Cl.
*C07K 1/00* (2006.01)
*A61K 38/16* (2006.01)

(52) U.S. Cl.
USPC ........................................ 530/360; 514/5.7

(58) Field of Classification Search
None
See application file for complete search history.

(56) References Cited

U.S. PATENT DOCUMENTS

2002/0183400 A1  12/2002  Baldo et al.
2004/0116386 A1*  6/2004  Pifferi et al. .................... 514/78

FOREIGN PATENT DOCUMENTS

| JP | 2005-514945 | 5/2005 |
| WO | 2004/035013 | 4/2004 |
| WO | 2004/103265 | 12/2004 |
| WO | WO2007122613 A1 * | 11/2007 |
| WO | WO 2007122613 A1 * | 11/2007 |

OTHER PUBLICATIONS

Yoon et. al. Inhibition of protein kinase CKII activity by resveratrol, a natural compound in red wine and grapes; Life Sciences, (71) 2145-2152, 2002, See p. 2149.*
California Polytechnic State University, Dairy Products Technology Center, Particle sizes of Milk Powders, Dairy Ingredients Fax, Part I, vol. 2, No. 4, Apr. 2000).*
International Search Report for PCT/EP2007/006821, mailed Sep. 27, 2007.
Written Opinion of the International Searching Authority for PCT/EP2007/006821, mailed Sep. 27, 2007.

* cited by examiner

*Primary Examiner* — Christina Bradley
*Assistant Examiner* — Jeanette Lieb
(74) *Attorney, Agent, or Firm* — Nixon & Vanderhye P.C.

(57) ABSTRACT

Complexes comprising resveratrol and a casein, a process for their manufacture, their uses and compositions comprising them.

13 Claims, No Drawings

CASEIN COMPLEXES

This application is the U.S. national phase of International Application No. PCT/EP2007/006821, filed 2 Aug. 2007, which designated the U.S. and claims priority to European Application No. 06016660.0, filed 9 Aug. 2006, the entire contents of each of which are hereby incorporated by reference.

The present invention relates to casein complexes. More precisely the present invention relates to complexes comprising casein and resveratrol, to a process for the manufacture thereof, to their uses and to compositions comprising them. Preferably complexes comprising casein and resveratrol are casein resveratrol complexes.

Resveratrol which by systematic name is 3,4',5-trihydroxystilbene is a known, naturally occurring compound which has gained much interest during the last years in view of its valuable biological properties and pharmacological effects. Resveratrol has been reported to exhibit many therapeutic as well as disease preventive qualities including being the reason for the so-called "French Paradox". The French Paradox is the fact that in people living on a mediterranean diet, containing high levels of fat and alcohol, an increase to be expected in cancer and heart diseases is not observed. Effects of resveratrol in various cellular and animal assays have been shown, e.g., with respect to inhibition not only of skin tumors and leukemia but also of platelet aggregation and coagulation. In addition resveratrol has been shown to be a vasorelaxant, an antimicrobial and fungicidal agent. Recently, data has been published demonstrating that resveratrol is capable of extending the longevity of mice fed a high fat diet.

Therefore, resveratrol is becoming more and more a compound useful not only in the prevention and therapy of specific illnesses and syndromes but for improving generally the health status, physically, mentally and beyond of mammals, preferably humans. This triggers the necessity to make available resveratrol in stable (physical, chemical, colour, taste) forms and formulations having a long shelf-life and improved solubility, especially in aqueous media which will allow its broad application, e.g., in food, feed, pharmaceuticals and cosmetics, especially in beverages.

Resveratrol has a very low solubility/dispersability in water which makes it difficult if not impossible to prepare concentrated stock solutions with good stability over a long time period normally used in the beverage industry for the manufacture of final clear solutions with concentrations of about 10-20 mg/240 ml of resveratrol.

It is an object of the present invention to overcome these difficulties and to provide a physical form of resveratrol which allows its broad application in many fields of technique, especially in the food and beverage industry. It has now surprisingly been found that these difficulties can be overcome by using resveratrol in the form of complexes with casein.

Therefore, the main aspect of the present invention relates to complexes of resveratrol with casein.

The term "resveratrol" as used herein in its broadest sense comprises resveratrol itself, in its trans as well as in its cis form, physiologically acceptable derivatives, metabolites and analogues thereof. In a preferred embodiment the term "resveratrol" comprises compounds encompassed by the general formula

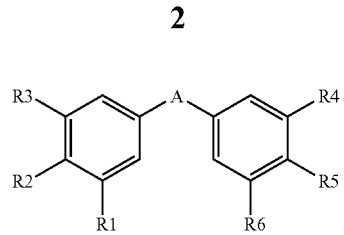

I wherein A denotes a carbon-carbon single or double bond which latter may be trans or cis, and R1, R2, R3, R4, R5 and R6, independently from each other denote hydrogen, hydroxy, etherified hydroxy or esterified hydroxy groups. Preferred are compounds I wherein A is a double bond (—CH═CH—).

While the carbon-carbon double bond denoted by the symbol A may be trans or cis, formula I above is understood to also include cis/trans mixtures. However, compounds of formula I wherein A is a trans carbon-carbon bond are preferred.

Etherified or esterified hydroxy groups may be derived from unsubstituted or substituted, straight or branched chain alkyl groups having 1 to 26 carbon atoms or from unsubstituted or substituted, straight or branched chain aliphatic, araliphatic or aromatic carboxylic acids having 1 to 26 carbon atoms. Etherified hydroxy groups may further be glycoside groups and esterified hydroxy groups may further be glucuronide or sulfate groups. Examples of compounds of formula I wherein A is —CH═CH— are resveratrol (R1, R3 and R5=hydrogen, R2, R4 and R6=hydroxy); piceatannol (R3 and R5=hydrogen, R1, R2, R4 and R6=hydroxy), and rhapontigenin (R5=hydrogen, R1, R3, R4 and R6=hydroxy, and R2=methoxy). Examples of compounds of formula I wherein A is —CH$_2$—CH$_2$— are dihydroresveratrol (R1, R3 and R5=hydrogen; R2, R4 and R6=hydroxy), dihydropiceatannol (R3 and R5=hydrogen; R1, R2, R4 and R6=hydroxy) and tristin (R3 and R5=hydrogen; R2, R4 and R6=hydroxy and R1=methoxy). These compounds are all well known and commercially available or can be obtained in accordance with methods well-known in the art.

For the purposes of the invention, resveratrol may be of natural or synthetic origin. In both cases the trans isomer is predominant, in the latter case nearly exclusively.

Metabolites of resveratrol are for instance dihydroresveratrol, piceatannol, dihydropiceatannol and tristin (3-methyl-dihydropiceatannol).

The resveratrol components of the present invention can be prepared synthetically or semi-synthetically using classical chemical synthesis or microbiological processes including genetic engineering and transformants or can be of natural origin which means that it is obtained from natural sources, e.g., grape seed, peanuts, or giant knotweed extract, in more or less concentrated and purified form. Furthermore, resveratrol may be used as a single active compound or as a mixture of two or more compounds as defined hereinbefore.

The term "casein" as used herein relates to all members of the fractions of milk proteins designated caseins, known to a person skilled in the art, comprising alpha-, beta-, gamma-, kappa- and lambda-caseins as sub-groups, taken individually or in the form of naturally occurring or synthetically prepared mixtures thereof. Within these sub-groups a multitude of genetic variations exist depending on the type and breed of animal as source of the milk. In connection with the present invention milk from all kinds of mammals including humans can be used as source of the casein. The preferred source is milk from cows. The casein proteins apart from being distinguished by their amino acid sequences and their tendency to form dimmers, trimers and higher oligomers, are carrying different amounts of phosphate and carbohydrate groups. Among the carbohydrate groups are galactose, galactosamine and N-acetyl-neuraminic acid groups. The term "casein" as used herein also comprises salts of the casein proteins with bases among which salts with alkali metals (sodium, potassium) and alkaline earth metals (calcium) and ammonium salts are preferred. Kappa-casein which normally occurs as a trimer or higher oligomer wherein the peptide chains are connected via sulfur bridges is the only main casein component which is soluble in the naturally occurring concentrations of milk in the presence of calcium ions. Furthermore kappa-casein can protect those casein fractions which are precipitable with calcium ions against such precipitation by building complexes. Gamma-caseins are degradation products of beta-caseins by proteolytic enzymes of milk while lambda-caseins mainly contain fragments of α-caseins which are obtainable in vitro by incubation of alpha-casein with plasmin (an alkaline cow proteinase). Therefore, the term "casein" as used in connection with the present invention also encompasses fragments or hydrolysates of caseins which are obtained by hydrolysis including enzymatic cleavage of complete long-chain caseins. While enzymatic cleavage is a site selective cleavage yielding generally well-defined fragments, hydrolysis under acidic or alkaline conditions yield less well-defined mixtures of shorter peptide chains. The degree of hydrolysis (DH) can vary considerably and can have any value between 1 and 70%, preferably between 1 and 10, 15, 20, 25, 30 or 35% which means that the respective number of peptide bonds in % is broken. Under carefully controlled hydrolytic degradation conditions mixtures of peptides with a typical molecular weight distribution are obtained.

An example of a casein hydrolysate which is highly nutritious and also suitable as a protein source in infant formulas with reduced allergen content is PEPTIGEN® IF-2050 of Arla Foods Ingredients, Viby, Denmark, which consists of short-chained peptides with a low bitterness profile, obtained by a carefully controlled enzymatic degradation. Its DH is 22-27 and its mean MW (Dalton) is 850-1200 (less than 1500:81, 7%; 1500-3500:17.2; 3500-6000:1.1% (w/w)).

In a preferred embodiment of the present invention naturally occurring-casein and hydrolysates thereof are used.

Many different kinds of caseins mentioned above useful in the practice of the present invention are commercially available and known under different trade marks. On the other hand, in accordance with well-known classical methods casein can be obtained by precipitation from skim milk with acids (e.g., HCl, $H_2SO_4$, $H_3PO_4$, lactic acid), at temperatures in the range of from 35-50° C. and a pH of 4.2-4.6, by fermentation with lactic acid producing microorganisms or by addition of proteinases (pepsin or rennin), isolation of the precipitate, washing and drying. Alkali and alkaline earth metal salts of caseins (viz. caseinates) can be obtained by neutralizing acidic casein solutions to pH 6.7 with sodium, potassium or calcium hydroxide solutions. An example of a commercially available potassium caseinate is MIPRODAN® 55, from Arla Food Ingredients, Viby, Denmark, which is manufactured from fresh pasteurized skimmed milk by acid precipitation of the casein, direct neutralization and spray-drying.

The weight ratio of resveratrol:casein in the casein complexes of the present invention is in the range of about 0.1:99.9-50:50, preferably in the range of 1:98-1:2. and can be, e.g., 3:97, 5:95 or 15:85.

A further aspect of the present invention is a process for the manufacture of the casein complexes defined above as aqueous solutions, preferably in concentrated form, or dry substances. This process can be performed in a manner known per se and comprises mixing a solution or dispersion of resveratrol, preferably in a water-mixable organic solvent, in which resveratrol has significant solubility or in a mixture of such solvent with water, with an aqueous solution of a casein in the desired weight ratio in a suitable mixing equipment, if desired under heating and, if desired, transforming the resulting solution into a concentrated aqueous solution or dry powder. Alternatively, resveratrol may be simply added to a casein-containing composition whereby a resveratrol—casein complex is formed. The term "concentrated solution" means a solution wherein the concentration of resveratrol is higher than in non-complexed form. Water-mixable organic solvents are polar solvents such a mono- di- or polyvalent alcohols (e.g., methanol, ethanol, propanol, iso-propanol, a butanol, etc., or glycerol), ketones like acetone or even dimethylformamide. Physiologically acceptable organic solvents and solvents approved for use in food and feed technology are preferred. Preferably the resveratrol solution is slowly added to the aqueous casein solution under stirring.

The organic solvent can be removed and the remaining aqueous solution can be concentrated by methods which are known to a person skilled in the art, e.g., by vaporization or evaporation, and then, if desired, the concentrate is transferred into a dry powder by well-known drying methods, e.g., convection, contact, freeze or spray drying in suitable equipments, if desired under concomitant or subsequent fragmentation, e.g., grinding. In the case of discrete powder particles of the complexes the average particle size or diameter is in the range of from 5-2000 µm. In dispersions, particularly in aqueous dispersions, the primary particle size, i.e., not aggregated, is normally in the range of 50-3000 nm, preferably below 250 nm, e.g., in the range of 100-250 nm or 50-250 nm. For tablet application a preferred particle size is 100-850 µm.

In a further aspect the present invention relates to a method for increasing the solubility/dispersability and stability of resveratrol in an aqueous environment by adding it in the form of a casein complex to the environment or as non-complexed compound to a casein-containing environment or adding casein to a resveratrol-containing environment.

An aqueous environment may be aqueous solutions or water-containing compositions. Casein-containing environments comprise products which contain or which are enriched with casein.

The casein complexes of resveratrol of the present invention can be used in the same ways and in the same application forms and formulations which are already known for resveratrol as an agent with various beneficial activities described in the literature, including its ability to improve the general physical and/or mental status of mammals, particularly humans Consequently, the present invention also relates to compositions comprising casein complexes of resveratrol in solid and dispersed/solved form, e.g., as free flowing powders or dispersions/solutions, preferably aqueous dispersions/solutions, for use as active agents in pharmaceutical and cosmetic preparations and in supplements for food and feed, including beverages as well as to pharmaceutical and cosmetic preparations, food and feed supplements and food and feed themselves containing these complexes as single active components or in combination with one or more other physiologically active components.

In a preferred aspect the present invention relates to beverages, containing the resveratrol casein complexes of the present invention in the form of stable solutions, i.e., with no ringing or precipitation, preferably in the form of optically clear solutions, in nutritionally supplemental amounts. Such amounts are in the range of from 20 mg/l-2000 mg/l.

The term "beverages" comprises all kinds of drinkable water, such as natural or artificial mineral waters, soft drinks, mineral drinks, sport drinks, fruit juices, fruit punches, fruit nectars, in concentrated as well as in diluted forms. The beverages may contain carbon dioxide, fruit and fruit flavors, water—as well as fat-soluble vitamins and nutritionally important minerals and trace elements, all artificial or of natural origin. By way of example, the fruit in the fruit juices and fruit flavors include the following: grape, pear, passion fruit, pineapple, banana, apricot, orange, lemon, lime, grapefruit, apple, cola, cranberry, tomato, mango papaya, tangerine, nectarine, plum, cherry, raspberry and carrot. Any combinations of these fruit and flavors are possible including chocolate and other non-fruit flavors. Also any kind of milk is comprised by the term "beverage" and may be fortified with the resveratrol complexes of the present invention.

The manufacture of the nutraceutical compositions of the present invention, viz. the galenical and cosmetic formulations and the food, feed and beverage supplements on the basis of resveratrol as active component can be performed in accordance with known methods in the art using the physiologically acceptable recipients. The nutraceutical compositions of the present invention contain resveratrol in an amount sufficient to administer to a human adult (body weight about 70 kg) a dosage from about 0.5 mg/day to about 2000 mg/day, preferably from about 5 mg/day to about 500 mg/day.

Thus, if the nutraceutical composition is a food or beverage the amount of the resveratrol contained therein is suitably in the range of from 0.2 mg to about 500 mg per serving. If the nutraceutical composition is a pharmaceutical formulation such formulation may contain from about 0.5 mg to about 500 mg per solid dosage unit, e.g., per capsule or tablet or from about 0.5 mg per daily dose to about 2000 mg per daily dose of a liquid formulation.

The following examples illustrate the present invention in more detail.

EXAMPLE 1

Solution A: 27.1 g of potassium caseinate with a moisture content of 7.54% (Miprodan® 55, Arla Foods, DK) were dissolved in 181.2 g of deionized water.

Solution B: 1.5 g of resveratrol (DSM Nutritional Products, CH) were dissolved in 70 g of ethanol at 40° C. and 35 g of deionized water were added to the solution.

208.3 g of solution A was added slowly to 106.5 g of solution B with stirring at 40° C. Ethanol was then removed by rotary evaporation. The remaining aqueous mixture (about 208 g) was dried with a spray-dryer (Niro Mobile Minor 2000, Copenhagen, DK) at inlet temperature of 209° C. and outlet temperature of 105° C. to yield a powder with a content of about 5.1% resveratrol based on UV analysis. 1,035 g of this powder was dispersed in deionized water to make up a 500 ml dispersion with an average particle size of 127-130 nm, a turbidity of 44.8 NTU and a resveratrol concentration of 119 ppm after 3 days.

EXAMPLE 2

Solution A: 34.4 g of potassium caseinate with a moisture content of 6.44% (Miprodan® 55, Arla Foods, DK) were dissolved in 235.6 g of deionized water.

Solution B: 3.68 g of resveratrol (DSM Nutritional Products, CH) were dissolved in 156 g of ethanol at room temperature.

159.7 g of solution B were added to 270 g of solution A with stirring. The mixture was placed in a rotary evaporator round-bottom flask and rotated in a 55° C. water bath for 1 hour without vacuum. The ethanol in the mixture was then removed under vacuum by rotary evaporation. The remaining aqueous mixture (about 250 g) was dried with a spraydrier (Niro Mobile Minor 2000, Copenhagen, DK) at inlet temperature of 199° C. and outlet temperature of about 92° C. to yield a powder with a content of about 10% resveratrol. 0.21 g of this powder were dispersed in 200 ml of water. After pasteurization and storage in the dark at room temperature for 4 weeks the sample was analyzed, the resveratrol concentration being 89.2 ppm.

EXAMPLE 3

Solution A: 34.4 g of potassium caseinate with 6.44% moisture content (Miprodan® 55, Arla Foods, Copenhagen, DK) were dissolved in 235.6 g of deionized water.

Solution B: 3.68 g of resveratrol (DSM Nutritional Products, CH) were dissolved in 156 g of ethanol at room temperature.

159.7 g of solution B were added slowly to 270 g of solution A with stirring. The mixture was placed in a rotary evaporator round-bottom flask and rotated in a 50° C. water bath for 1 hour without vacuum. The ethanol and most of the water in the mixture were then removed under vacuum by rotary evaporation to give a gummy material containing about 6.05% resveratrol. 1,050 g of this material were dispersed in 50° C. deionized water to make up a 1000 ml dispersion. After cooling down to room temperature the pH was adjusted to 6.5 with 0.1 N HCl. The mixture was then filled in glass bottles and pasteurized at 70° C. for 20 minutes. The samples were stored in dark at room temperature for 6 weeks. Particle size, turbidity and resveratrol concentration (by UV) were determined to be 215 nm, 25.6 NTU and 63.3 ppm, respectively.

EXAMPLE 4

Solution A: 15.3 g of potassium caseinate with a moisture content of 6.44% (Miprodan® 55, Arla Foods, Copenhagen, DK) were dissolved in 236.7 g of deionized water.

Solution B: 3.68 g of resveratrol (DSM nutritional Products, CH) were dissolved in 156 g of ethanol at room temperature.

159.7 g of solution B were added slowly to 252 g of solution A with stirring. The mixture was placed in a rotary evaporator round-bottom flask and rotated in a 50° C. water bath for 1 hour without vacuum. The ethanol and water in the mixture were then removed under vacuum by rotary evaporation at 50° C. The residue was further dried in a 10% humidity box and then in a vacuum oven till dryness and then ground to powder. 1,050 g of the powder were dispersed in 200 ml of deionized water and the mixture was then pasteurized at 70° C. for 20 minutes. The dispersion was placed in glass bottles and stored in dark. After one day the particle size, turbidity and resveratrol concentration (By UV) were determined to be 259 nm, 11.4 NTU and 100.6 ppm, respectively.

EXAMPLE 5

Solution A: 11.55 g of potassium caseinate with a moisture content of 6.44% (Miprodan® 55, Arla Foods, Copenhagen, DK) were dissolved in 278 deionized water.

Solution B: 3.68 g of resveratrol (DSM Nutritional Products, CH) were dissolved in 156 g of ethanol at room temperature.

159.7 g of solution B were added slowly to 289.6 g of solution A with stirring. The resulting mixture was placed in a rotary evaporator round-bottom flask and rotated in a 50° C. water bath for 1 hour without vacuum. The ethanol and water were then removed from the mixture under vacuum (15 mbar) by rotary evaporation at 50° C. The residue was further dried at 40° C. in a vacuum oven till dryness and the ground to powder.

0.263 g of the powder were dispersed in 1000 ml of 70° C. deionized water. A 200 ml sample was filled in a glass bottle and heated at 70° C. for 20 minutes (not completely dispersed) and again at 90° C. for 20 minutes until complete dispersion. The particle size, turbidity and resveratrol concentration (By UV) were determined to be 244.9 nm, 13.8 NTU and 106.5 ppm, respectively.

EXAMPLE 6

Solution A: 30.2 g of potassium caseinate with a moisture content of 6.44% (Miprodan*55, Arla Foods, Copenhagen, DK) were dissolved in 250 g of deionized water.

159.7 g of solution A were mixed with 1.84 g of resveratrol. The mixture was heated in a round-bottom flask at 75° C. in a water bath for 1.5 hours and the material was transferred to a beaker and heated with magnetic stirring in 90°-95° C. water bath for 2 hours. The paste was dried in a vacuum oven at 40° C. overnight. The powder contained about 4.82% resveratrol. 2,178 g thereof were dispersed in 1000 ml of deionized water, adjusted to pH 6.5 and then pasteurized at 75° C. for 20 minutes. Particle size was 213 nm, turbidity 33.3 NTU and the resveratrol concentration 107 ppm.

EXAMPLE 7

Solution A: 60.6 g of casein hydrolyzate (Peptigen® IF-2050, Arla Foods, DK) with a moisture content of 6.71% were dissolved in 235 g of deionized water.

Solution B: 3.68 g of resveratrol (DSM Nutritional Products, CH) were dissolved in 156 g of ethanol.

159.68 g of solution B were added slowly to 295.6 g of solution A with stirring. The mixture was transferred to a round bottom flask and rotated in a 50° C. water bath for 1 hour in a rotary evaporator without vacuum and then dried under vacuum. The dry material was ground into powder.

The powder (20 g) was dispersed in deionized water (180 g, pH 6.8) and stirred for 15 minutes. 32 g of the dispersion were added to 2268 g of deionized water and the pH of 6.2 was adjusted to 6.8 with diluted sodium bicarbonate solution. The dispersion was heated in a 95° C. water bath for 20 minutes. After cooling to room temperature, a clear resveratrol dispersion containing 70 ppm of resveratrol was obtained. After storage at 25° C. for 1 week, the solution remained clear and still contained 70 ppm of resveratrol.

EXAMPLE 8

Solution A: 60.4 g of potassium caseinate with a moisture content of 6044% (Miprodan® 55, Arla Foods, Copenhagen, DK) were dissolved in 500 g of deionized water.

Solution B: 3.68 g of resveratrol (DSM Nutritional Products, CH) were dissolved in 156 g of ethanol.

159.68 g of solution B were added slowly to solution A (560.4 g) with stirring. The mixture was transferred to a round bottom flask and heated in a 50° C. water bath for 1 hour with rotation in a rotary evaporator without vacuum and then dried under vacuum. The dry material was further dried in a vacuum oven at 40 C. overnight. The oven-dried materials was ground into powder.

The powder (2.5 g) was dispersed in deionized water (47.5 g) with stirring. The dispersion was centrifuged at 3000 rpm for 5 minutes (Sigma Centrifuge 6-10, Sigma Laborzentrifugen GmbH, Germany) to remove the un-dispersible material. The supernatant was lyophilized to yield 1.7 g powder. The powder (1 g) was suspended in deionized water (9 g) to give a 10% homogenous dispersion. A sample of the dispersion was placed in a test tube and stored at room temperature for 3 hours and then at 5° C. for 1 day. A small sample was taken from the upper part of the test tube and then a sample was taken after mixing. The resveratrol content of the sample taken from the upper part of the test tube and the sample taken after mixing contained 0.422% and 0.425% resveratrol, respectively. The results indicated the dispersion stability. The highly concentrate dispersion can be conveniently used for various applications in pharmaceuticals and cosmetics, food and feed, especially in beverages.

This example shows the advantage of the resveratrol complex over non-complexed resveratrol (neat resveratrol). A dispersion of more than 0.005% (likely much less using similar dispersion conditions) of non-complexed resveratrol would result in precipitation of resveratrol.

EXAMPLE 9

Resveratrol-caseinate complex used was the oven-dried material described in Example 8 (non-dispersible material was not removed by centrifugation). Crystalline resveratrol was included for comparison.

Complexed and crystalline resveratrol was dispersed in deionized water of pH 6.8 or 3.0 to give a final target dispersion concentration of 60 and 80 ppm. The desired pH was achieved by pH adjustment using dilute HCl or NaHCO₃ The samples were heated in a water bath till 80° C. and then held at 80° C. for 1 minute. The samples were stored in the dark at 25° C. and 5° C. During storage, resveratrol recrystallized and precipitated in some samples. The resveratrol concentration in the supernatant were determined by a UV method and the results are shown below,

|  | pH | Temp, C. | Resveratrol in supernatant, ppm | | |
|---|---|---|---|---|---|
|  |  |  | Initial | 1 week | 2.4 week |
| Resveratrol | 6.8 | 25 | 60 | 45 (75%) | 39 (65%) |
| Resveratrol | 6.8 | 5 | 60 | 23 (38%) | 17 (28%) |
| Resveratrol | 3.0 | 25 | 58 | 43 (74%) | 39 (67%) |
| Resveratrol | 3.0 | 5 | 58 | 28 (48%) | 19 (33%) |
| Resveratrol-caseinate | 6.8 | 25 | 60 | 61 (100%) | 58 (97%) |
| Resveratrol-caseinate | 6.8 | 5 | 60 | 59 (98%) | 58 (98%) |
| Resveratrol-caseinate | 3.0 | 25 | 59 | 61 (100%) | 59 (100%) |
| Resveratrol-caseinate | 3.0 | 5 | 59 | 60 (100%) | 57 (97%) |
| Resveratrol | 6.8 | 25 | 79 | 45 (57%) | 43 (54%) |
| Resveratrol | 6.8 | 5 | 79 | 24 (30%) | 16 (20%) |
| Resveratrol | 3.0 | 25 | 80 | 47 (59%) | 38 (48%) |
| Resveratrol | 3.0 | 5 | 80 | 28 (35%) | 16 (20%) |
| Resveratrol-caseinate | 6.8 | 25 | 80 | 82 (100%) | 79 (99%) |
| Resveratrol-caseinate | 6.8 | 5 | 80 | 82 (100%) | 81 (100%) |
| Resveratrol-caseinate | 3.0 | 25 | 79 | 78 (99%) | 77 (98%) |
| Resveratrol-caseinate | 3.0 | 5 | 79 | 76 (96%) | 42 (53%) |

EXAMPLE 10

Preparation of a Beverage with 10% Juice a) 10% Stock-Solution Resveratrol Complex Add 10 g of the resveratrol complex (6% resveratrol) to 90 g of deionised water and stir.

b) Juice Compound

Add 328.4 g of deionised water to 483.3 g of orange juice concentrate (65° Brix) and 173.3 g of lemon juice concentrate (45° Brix). Stir gently and allow the juice concentrates to hydrate. Add 5 g of oily orange flavour and 10 g of beta-carotene (10% CWS form DSM) as a 10% stock solution and pre-emulsify in a rotor-stator-homogeniser. Homogenise the juice compound in a high pressure homogeniser.

c) Beverage Preparation 0.2 g of sodium-benzoate is dissolved in 100 ml of deionised water. Afterwards 156.2 g of sugar syrup (64° Brix), 0.4 g of ascorbic acid fine powder, 5 g of citric acid (50% w/w solution), 10 g of pectin solution (2% w/w), 30 g of juice compound and 13.3 g of 10% resveratrol complex stock solution are added under stirring, one after the other. The syrup is then filled up to 1 liter of beverage with tap or carbonated water.

EXAMPLE 11

Preparation of a Beverage with 10% Juice a) 10% Stock-Solution Resveratrol Complex Add 50 g of the resveratrol complex (6% resveratrol) to 450 g of deionised water and stir.

b) Juice Compound

Add 328.4 g of deionised water to 483.3 g of orange juice concentrate (65° Brix) and 173.3 g of lemon juice concentrate (45° Brix). Stir gently and allow the juice concentrates to hydrate. Add 5 g of oily orange flavour and 10 g of beta-carotene (10% CWS form from DSM) as a 10% stock solution and pre-emulsify in a rotor-stator-homogeniser. Add 444.4 g of 10% resveratrol complex stock solution. Homogenise the juice compound in a high pressure homogeniser.

c) Beverage Preparation 0.2 g of sodium-benzoate is dissolved in 100 ml of deionised water. Afterwards 156.2 g sugar syrup (64° Brix), 0.4 g of ascorbic acid fine powder, 5 g of aqueous citric acid solution (50% w/w), 10 g of pectin solution (2% w/w) and 30 g of juice compound are added under stirring, one after the other. The syrup is then filled up to 1 liter of beverage with tap or carbonated water.

EXAMPLE 12

Preparation of a Near Water Drink

Dissolve 0.2 g of sodium-benzoate in 100 ml deionised water. Add 0.4 g of ascorbic acid, 7.2 g of sugar, 2 g of citric acid (50% w/w aqueous solution), 0.1 g of water-soluble ginger ale flavour and 0.2 g of water-soluble lemon flavour and stir. Add 13.3 g of 10% resveratrol stock solution (see Example 10a) and stir. Fill up to 1 liter of beverage with tap or carbonated or mineral water.

The invention claimed is:

1. A complex comprising resveratrol and a casein, wherein the weight ratio of resveratrol:casein component is 1:98 to 1:2.

2. A complex of claim 1 wherein the casein is a casein alkali, alkaline earth metal or ammonium salt or a casein hydrolysate.

3. A complex of claim 1 in the form of discrete powder particles with an average particle diameter of from 5 to 2000 µm.

4. A complex of claim 1 as a supplement for food, feed or as a component of pharmaceutical or cosmetic preparations.

5. A complex of claim 1 in the form of a dispersion.

6. The complex of claim 5 wherein the primary particle size is in the range of 50-3000 nm.

7. A composition comprising a complex according to claim 1.

8. A food or feed containing a complex as claimed in claim 1.

9. A beverage containing a complex as claimed in claim 1.

10. A pharmaceutical or cosmetic preparation containing a complex as claimed in claim 1 and a physiologically acceptable carrier.

11. The complex of claim 1, wherein the weight ratio of resveratrol casein component is 3:97.

12. The complex of claim 1, wherein the weight ratio of resveratrol:casein component is 5:95.

13. A complex comprising resveratrol and a casein, wherein the weight ratio of resveratrol:casein component is 5.50:94.4 or 25.35:74.65.

* * * * *